United States Patent [19]

Kubota et al.

[11] Patent Number: 5,362,724
[45] Date of Patent: Nov. 8, 1994

[54] THIOALKYLTHIO CARBACEPHALOSPORIN DERIVATIVES

[75] Inventors: Tadatoshi Kubota, Habikino; Masaharu Kume, Amagasaki, both of Japan

[73] Assignee: Shionogi & Co., Ltd., Osaka, Japan

[21] Appl. No.: 128,770

[22] Filed: Sep. 17, 1993

[30] Foreign Application Priority Data

Sep. 30, 1992 [JP] Japan .................. 4-261478

[51] Int. Cl.⁵ .................. C07D 471/04; A61K 31/435
[52] U.S. Cl. .................. 514/210; 540/205
[58] Field of Search ......... 540/226, 227, 205; 514/210

[56] References Cited

U.S. PATENT DOCUMENTS 4,123,528 10/1978 Cama et al. .............. 424/248.52
4,760,060 7/1988 Mochida et al. ............... 540/205
5,214,037 5/1993 Kubota et al. ............... 540/227

FOREIGN PATENT DOCUMENTS 0154253 9/1985 European Pat. Off. .
0182301 5/1986 European Pat. Off. .
0467647 1/1992 European Pat. Off. .

Primary Examiner—Nicholas Rizzo
Attorney, Agent, or Firm—Wenderoth, Lind & Ponack

[57] ABSTRACT

A compound of the formula I:

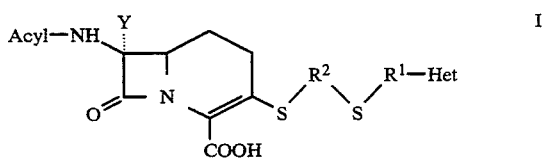

wherein Acyl is $C_1$-$C_{12}$ acyl; Het is an optionally substituted monocyclic heteroaromatic group containing one or more hetero atoms; $R^1$ is a single bond or $C_1$-$C_4$ alkylene; $R^2$ is a straight or branched $C_1$-$C_4$ alkylene; and Y is a hydrogen atom or methoxy group, or a pharmaceutically acceptable salt or an amino-, carboxy- and/or hydroxy-protected derivative thereof, which have a potent antibiotic activity.

13 Claims, No Drawings

THIOALKYLTHIO CARBACEPHALOSPORIN DERIVATIVES

FIELD OF THE INVENTION

This invention relates to novel β-lactam antibiotics, more specifically, it relates to thioalkylthio carbacephalosporin derivatives, processes for producing said compounds, antibiotic formulations which contain, as an active ingredient, a compound of the invention, and methods for combating bacteria or treating bacterial infections.

BACKGROUND OF THE INVENTION

The β-lactam antibiotics constitute a very useful family of antibiotics owing to their broad antibacterial spectrum. The present inventors have developed orally effective cephalosporin derivatives which have, at the 3-position of the cephem nucleus, a thioalkylthio side chain substituted by a heterocyclic group, disclosed in U.S. patent application Ser. No. 07/729,413, filed on Jul. 12, 1991, (now U.S. Pat. No. 5,214,037) and EPO Application Publication No. 0 467 647 A2, (Jan. 22, 1992). However, because of the increase in low-sensitive bacteria or the appearance of resistant bacteria, further development of effective antibiotics is continuously needed.

The present inventors have made intensive studies with the purpose of developing novel and effective antibiotics and synthesized thioalkylthio carbacephalosporin derivatives having at the 3-position of the 1-carbacephem nucleus a thioalkylthio side chain optionally substituted by a heterocyclic group, said derivatives corresponding to those disclosed in the aforementioned U.S. patent application Ser. No. 07/729 413, now U.S. Pat. No. 5,214,037 and EPO Application Publication No. 0 467 647 A2 (Jan. 22, 1992). When these carbacephalosporin derivatives were evaluated for antibiotic properties, certain compounds, for example, those having a thioalkylthio side chain substituted with an optionally substituted triazolyl, showed preferable properties in terms of antibiotic activity, binding ability to plasma proteins and the like.

SUMMARY OF THE INVENTION

Thus, the present invention provides a compound of the formula I:

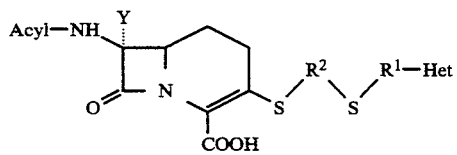

wherein Acyl is $C_1$-$C_{12}$ acyl; Her is optionally substituted monocyclic heteroaromatic group containing one or more hetero atoms; $R^1$ is a single bond or $C_1$-$C_4$ alkylene; $R^2$ is a straight or branched $C_1$-$C_4$ alkylene; and Y is a hydrogen atom or methoxy group, or a pharmaceutically acceptable salt or an amino-, carboxy- and/or hydroxy-protected derivative thereof.

As can be seen from the formula above, the compound of the invention can form a salt with a base commonly used in the field of β-lactam antibiotics. It is also appreciated that amino, carboxy, and hydroxy groups contained in Her and Acyl groups of the molecule may be protected by protecting groups useful to prevent a compound from varying in the course of production and/or formulation, or while being stored. Many protecting groups are known to one of ordinary skill in the art, which can be removed easily to render an active ingredient when administered or applied to a subject and/or are harmless to the living body and/or do not affect the pharmacological activity of an active ingredient.

Thus, the present invention provides a compound of formula I, a salt and a protected derivative thereof.

DETAILED DESCRIPTION OF THE INVENTION

For purposes of the present invention, as disclosed and claimed herein, the following terms are defined below.

In the definition of Het, the term "heteroaromatic group" refers to a 5- or 6-membered monocyclic ring which contains one or more, preferably 3 or 4 hetero atoms selected from nitrogen and/or sulfur. Specific examples are pyridyl, triazolyl such as 1,2,3- or 1,2,4-triazolyl, thiadiazolyl such as 1,2,3- or 1,2,4-thiadiazolyl, tetrazolyl and the like. The heteroaromatic groups may have one or more substituents selected from, for example, lower alkyl such as methyl, ethyl and the like. Especially preferable heteroaromatic groups are optionally substituted 1,2,3-triazolyl substituted with methyl.

In the definition of Acyl, the term "$C_1$-$C_{12}$ acyl" refers to an acyl group having 1 to 12 carbon atoms. Examples of $C_1$-$C_{12}$ acyl are alkanoyl, aralkanoyl and aroyl optionally having a substituent(s) of 1 to 15 carbon atoms. In the acyl group, an aryl moiety may be a heterocyclic group and, further, a functional group(s) may be protected by a protecting group(s) generally used in the field of cephalosporin. Preferred acyl groups are $C_1$-$C_8$ alkanoyl, $C_7$-$C_{11}$ aroyl, and 5- or 6-membered homo- or hetero-cyclic aralkanoyl, each of which may have a substituent(s). Examples of substituents include $C_1$-$C_5$ alkyl, $C_2$-$C_5$ carboxyalkyl, alkenyl, cycloalkenyl, amino, imino, hydroxyimino, $C_1$-$C_5$ alkyloxyimino, $C_1$-$C_5$ alkenyloxyimino, $C_3$-$C_5$ cycloalkyloxyimino, carboxy-$C_1$-$C_5$ alkylthio, hydroxy, oxo, $C_1$-$C_5$ alkoxy, halogen and the like. Preferred substituents are haloalkylthio, alkoxyimino, cyclic alkoxyimino, alkenyloxyimino, amino, protected amino, hydroxy, oxo, hydroxyimino, protected hydroxyimino, carboxyalkoxyimino, carboxyalkenyloxyimino and the like.

Typical examples of optionally substituted acyl include (Z)-(2-aminothiazol-4-yl)-2-hydroxyiminoacetyl, 2-(2-aminothiazol-4-yl)acetyl, α-phenylglycyl, D-mandeloyl, 2-(2-aminothiazol-4-yl)glyoxylyl, difluoromethylthioacetyl, (Z)-2-(2-aminothiazol-4-yl)-2-pentenoyl, (Z)-2-(2-aminothiazol-4-yl)-2-tetrahydropyranyloxyimino acetyl, (Z)-2-(2-aminothiazol-4-yl)-2-trityloxyiminoacetyl, (Z)-2-(2-aminothiazol-4-yl)-2-(2-propenyloxyimino)acetyl, (Z)-2-(2-aminothiazol-4-yl)-2-cyclopentyloxyiminoacetyl, (Z)-2-(2-aminothiazol-4-yl)-2-(carboxymethoxyimino)acetyl, (Z)-2-(2-aminothiazol-4-yl)-2-[(S)-1-carboxyethoxyimino)]-acetyl, (Z)-2-(1-carboxy-1-methylethoxyimino)acetyl, (Z)-2-(2-aminothiazol-4-yl)-2-(1-carboxyvinyloxyimino)acetyl, (Z)-2-(2-aminothiazol-4-yl)-2-(2-methoxyimino)-acetyl and the like. Especially preferred acyl is (Z)-2-(2-aminothiazol-4-yl)-2-hydroxyiminoacetyl wherein the hydroxyimino group is optionally modified with a conventional hydroxy-protecting group, $C_1$-$C_5$ alkyl, or $C_2$-$C_5$ carboxyalkyl.

The term "straight or branched $C_1$–$C_5$ alkylene" refers to methylene, ethylene, methylmethylene and the like.

As previously described, functional groups such as carboxyl, amino and hydroxyl groups may be conventionally protected by appropriate protecting groups commonly used in the field of β-lactam antibiotics.

Examples of carboxy-protecting groups usable in the present invention include those which are known and generally used in the field of penicillin and cephalosporin to protect a carboxyl group during reaction. Such protecting groups contain 1–19 carbon atoms and can bind to a carboxyl group reversibly without affecting the other parts of the molecule.

Typical examples include ester-forming groups such as $C_1$–$C_8$ alkyl (methyl, methoxymethyl, ethyl, ethoxymethyl, iodomethyl, propyl, isopropyl, butyl, isobutyl, ethoxyethyl, methylthioethyl, methanesulfonylethyl, trichloroethyl, t-butyl and the like); $C_3$–$C_8$ alkenyl (propenyl, allyl, prenyl, hexenyl, phenylpropenyl, dimethylhexenyl and the like); $C_7$–$C_{19}$ aralkyl (benzyl, methylbenzyl, dimethylbenzyl, methoxybenzyl, ethoxybenzyl, nitrobenzyl, aminobenzyl, diphenylmethyl, phenylethyl, trityl, di-t-butylhydroxybenzyl, phthalidyl, phenacyl and the like); $C_6$–$C_{12}$ aryl (phenyl, toluyl, diisopropylphenyl, xylyl, trichlorophenyl, pentachlorophenyl, indanyl and the like); $C_1$–$C_{12}$ amino which can form an ester with acetone oxime, acetophenone oxime, acetoaldoxime, N-hydroxysuccineimide, N-hydroxyphthalimide or the like; $C_3$–$C_{12}$ hydrocarbonated silyl (trimethylsilyl, dimethylmethoxysilyl, t-butyldimethylsilyl and the like); $C_3$–$C_{12}$ hydrocarbonated stannyl (trimethylstannyl and the like).

Other examples of carboxy-protecting groups are pharmaceutically active ester forming groups. Examples of such groups include 1-(oxgen-substituted)-$C_2$ to $C_5$ alkyl groups {a straight, branched, ringed, or partially ringed alkanoyloxyalkyl (acetoxymethyl, acetoxyethyl, propionyloxymethyl, pivaloyloxymethyl, pivaloyloxyethyl, cyclohexaneacetoxyethyl, cyclohexanecarbonyloxycyclohexylmethyl and the like); $C_3$–$C_{15}$ alkoxycarbonyloxyalkyl (ethoxycarbonyloxyethyl, isopropoxycarbonyloxypropyl, isopropoxycarbonyloxyethyl, t-butoxycarbonyloxyethyl, isopentyloxycarbonyloxypropyl, cyclohexyloxycarbonyloxyethyl, cyclohexylmethoxycarbonyloxyethyl, bornyloxycarbonyloxyisopropyl and the like); $C_2$–$C_8$ alkoxyalkyl (methoxymethyl, methoxyethyl and the like); $C_4$–$C_8$ 2-oxacycloalkyls (tetrahydropyranyl, tetrahydrofuranyl and the like) and the like}; substituted $C_8$–$C_{12}$ aralkyls, (phenacyl, phthalidyl and the like); $C_6$–$C_{12}$ aryl (phenyl, xylyl, indanyl and the like); $C_2$–$C_{12}$ alkenyl (allyl, isoprenyl, 2-oxo-1,3-dioxolyl-4-yl-methyl and the like) and the like.

As a carboxy-protecting group used to block the carboxyl group during reactions is usually removed at the final step of the reaction, such group can be selected, irrespective of the structure, from various equivalent groups including amides, acid anhydrides formed with carbonic acid or carboxylic acids and the like, as long as the objective carboxyl group is protected properly.

These protecting groups may have substituents.

Hydroxy-protecting groups which can be introduced and removed without causing any adverse effects on other parts of the molecule are also known in the field of β-lactam antibiotics. Typical examples of such groups include easily removable ester forming group, for example, $C_1$–$C_{10}$ carboxylic acyl (formyl, acetyl, propionyl, pivaloyl and $C_7$–$C_{10}$ aroyl such as benzoyl, toluoyl, xyloyl and the like); $C_1$–$C_{10}$ carbonic acyl (alkoxycarbonyl, trichloroalkoxycarbonyl, benzyloxycarbonyl, p-nitrobenzyloxycarbonyl, p-methoxybenzyloxy- carbonyl, o-nitrobenzyloxycarbonyl, allyloxycarbonyl and the like); easily removable $C_2$–$C_4$ ether forming group (tetrahydropyranyl, tetrahydrofuranyl, methoxymethyl, methoxyethoxymethyl and the like); $C_3$–$C_{18}$ hydrocarbylsilyl (trimethylsilyl, triethylsilyl, dimethylphenylsilyl, diphenyl-t-butylsilyl, dimethyl-t-pentylsilyl and the like), and $C_7$–$C_{19}$ reactive aralkyl (triphenylmethyl and the like).

Amino-protecting groups which can be introduced and removed without causing any adverse effects on other parts of the molecule are also known in the field of β-lactam antibiotics. Typical examples of such groups include $C_1$–$C_8$ alkyl (t-butyl, methoxymethyl, methoxyethoxymethyl, trichloroethyl, tetrahydropyranyl and the like); $C_7$–$C_{19}$ aralkyl (benzyl, methylbenzyl, benzhydryl, methoxybenzyl, nitrobenzyl and the like); $C_6$–$C_{12}$ arylthio (nitrophenylthio and the like); $C_1$–$C_8$ acyl [$C_1$–$C_8$ alkanoyl (acetyl, chloroacetyl, trifluoroacetyl and the like); $C_2$–$C_{12}$ alkoxycarbonyl having methyl, ethyl, propyl, cyclopropylmethyl, cyclopropylethyl, isoproyl, butyl, isobutyl, pentyl, hexyl, trichloroethyl, pyridylmethyl, cyclopentyl, cyclohexyl and the like as the alkyl part; $C_8$–$C_{19}$ aralkoxycarbonyl having benzyl, benzhydryl, nitrobenzyl and the like as the aralkyl part; $C_7$–$C_{15}$ aroyl (benzoyl, nitrobenzoyl and the like); $C_3$–$C_{10}$ acyl of a dibasic acid (succinyl, phthaloyl and the like); chlorosulfonyl; $C_0$–$C_{10}$ phosphoric acyl. (dialkoxyphosphoryl, dichlorophosphoryl and the like) and the like]; $C_3$–$C_9$ trialkylsilyl; $C_3$–$C_9$ alkoxydialkylsilyl; $C_1$ to $C_8$ alkylidene or $C_7$–$C_{14}$ aralkylidene (benzylidene, methylbenzylidene, nitrobenzylidene and the like). An acid addition salt can also be an amino-protected compound. One or two of the above protecting groups may bind to an amino group(s).

Typical compounds of formula I are listed below, however, these are shown for illustrative purpose only and are not intended to limit the scope of the invention.

7β-Difluoromethylthioacetamido-3-(1,2,3-triazol-4-ylthiomethylthio)-1-carba-3-cephem-4-carboxylic acid;

7β-Phenylacetylamino-3-(1,2,3-triazol-4-ylthiomethylthio)-1-carba-3-cephem-4-carboxylic acid;

7β-D-Mandelamido-3-(1,2,3-triazol-4-ylthiomethylthio)-1-carba-3-cephem-4-carboxylic acid;

7β-[(Z)-2-(2-Aminothiazol-4-yl)-2-pentenoylamino]3-(1,2,3-triazol-4-ylthiomethylthio)-1-carba-3-cephem-4-carboxylic acid;

7β-[(Z)-2-(2-Aminothiazol-4-yl)-2hydroxyiminoacetamido]-3-(1,2,3-triazol-4-ylthiomethylthio)-1-carba-3-cephem-4-carboxylic acid;

7β-[2-(2-Aminothiazol-4-yl)-2methoxyiminoacetyl]amino-3-(1,2,3-triazol--4-ylthiomethylthio)-1-carba-3-cephem-4-carboxylic acid;

7β-[(Z)-2-(2-Aminothiazol-4-yl)-2-cyclopentyloxyiminoacetamido]-3-(1,2,3-triazol-4-ylthiomethylthio)-1-carba-3-cephem-4-carboxylic acid;

7β-[(Z)-2-(2-Aminothiazol-4-yl)-2-(2-propenyloxyiminoacetamido]3-(1,2,3-triazol-4-ylthiomethylthio)-1-carba-3-cephem-4-carboxylic acid;

7β-(2-Phenylglycylamino)-3-(1,2,3-triazol--4-ylthiomethylthio)-1-carba-3-cephem-4-carboxylic acid;

7β-[2-(2-Aminothiazol-4-yl)acetamido]-3-(1,2,3-triazol-4-ylthiomethylthio)-1-carba-3-cephem-4-carboxylic acid;

7β-[2-(2-Aminothiazol-4-yl)glyoxylamido]-3-(1,2,3-triazol-4-ylthiomethylthio)-1-carba-3-cephem-4-carboxylic acid;

7β-[(Z)-2-(2-Amino-4-thiazolyl)-2-hydroxyiminoacetamido]-3-(1,2,3-triazol-4-ylthiomethylthio)-1-carba-3-cephem-4-carboxylic acid;

7β-[(Z)-2-(2-Aminothiazol-4-yl)-2-carboxymethoxyiminoacetamido]-3-(1,2,3-triazol-4-ylthiomethylthio)-1-carba-3-cephem-4-carboxylic acid;

7β-{(Z)-2-(2-Aminothiazol-4-yl)-2-[(S)-1-carboethoxyimino]acetamido}-3-(1,2,3-triazol-4-ylthiomethylthio)-1-carba-3-cephem-4-carboxylic acid;

7β-[(Z)-2-(2-Aminothiazol-4-yl)-2-(1-carboxyvinyloxyiminoacetamido]-3-(1,2,3-triazol-4-ylthiomethylthio)-1-carba-3-cephem-4-carboxylic acid;

7β-[(Z) -2-(2-Aminothiazol-4-yl)-2-(1-carboxy-1-methylethoxyimino)acetamido]-3-(1,2,3-triazol-4-ylthiomethylthio)-1-carba-3-cephem-4-carboxylic acid;

7β-[(Z) -2-(2-Aminothiazol-4-yl)-2-hydroxyiminoacetamido]-3-(1-methyl-1,2,3-triazol-4yl)thiomethylthio-1-carba-3-cephem-4-carboxylic acid;

7β-[(Z)-2-(2-Aminothiazol-4-yl)-2-hydroxyiminoacetamido]-3-(2-methyl-1,2,3-triazol-4yl)thiomethylthio-1-carba-3-cephem-4 -carboxylic acid;

7β-[(Z)-2-(2-Aminothiazol-4-yl)-2hydroxyiminoacetamido]-3-(3-methyl-1,2,3-triazol-4-yl)thiomethylthio-1-carba-3-cephem-4-carboxylic acid;

7β-[(Z)-2-(2-Aminothiazol-4-yl)-2hydroxyiminoacetamido]-3-(1,2,4-triazol-3-yl)thiomethylthio-1-carba-3-cephem-4-carboxylic acid;

7β-[(Z) -2-(2-Aminothiazol-4-yl)-2hydroxyiminoacetylamino]-3-(1-methyl-1,2,4-triazol-3-ylthiomethylthio)-1-carba-3-cephem-4-carboxylic acid;

7β-[(Z) -2-(2-Aminothiazol-4-yl)-2hydroxyiminoacetylamino]-3-(2-methyl-1,2,4-triazol-3 -yl-thiomethylthio)-1-carba-3-cephem-4-carboxylic acid;

7β-[(Z)-2-(2-Aminothiazol-4-yl)-2-hydroxyiminoacetylamino]-3-(4-methyl-1,2,4-triazol-3-ylthiomethylthio)-1-carba-3-cephem-4-carboxylic acid;

7β-[(Z)-2-(2-Aminothiazol-4-yl)-2-hydroxyiminoacetylamino]-3-(1,2,3-thiadiazol-5-yl)thiomethylthio)-1-carba-3-cephem-4-carboxylic acid;

7β-[(Z)-2-(2-Amino-4-thiazolyl)-2-hydroxyiminoacetamido]-3-(1,3,4-thiadiazol-2-ylthiomethylthio)-1-carba-3-cephem-4-carboxylic acid;

7β-[(Z)-2-(2-Aminothiazol-4-yl)-2hydroxyiminoacetamido]-3-(2-methyl-1,3,4-thiadiazol-5-ylthiomethylthio)-1-carba-3-cephem-4-carboxylic acid;

7β-[(Z)-2-(2-Aminothiazol-4-yl)-2hydroxyiminoacetylamino]-3-(5-tetrazolyl)thiomethylthio-1-carba-3-cephem-4-carboxylic acid;

7β-[(Z)-2-(2-Aminothiazol-4-yl)-2-hydroxyiminoacetylamino]-3-(1-methyl-5-tetrazolyl)thiomethylthio)-1-carba-3-cephem-4-carboxylic acid;

7β-[(Z)-2-(2-Aminothiazol-4-yl)-2-hydroxyiminoacetylamino]-3-(2-methyltetrazol-5-ylthiomethylthio)-1-carba-3-cephem-4-carboxylic acid; and 7β-[(Z)-2-(2-Aminothiazol-4-yl)-2-hydroxyiminoacetamido]-3-(2-pyridylthiomethylthio)-1-carba3-cephem-4-carboxylic acid.

The compounds I of the invention can be produced by any methods which are generally used in the field of β-lactam antibiotics including the preparation of 7-acyl side chain, 3-substituent and cephem nucleus, introduction of a 7-acyl side chain and a 3-substituent to a cephem nucleus, deprotection, salt-formation, neutralization and the like. However, the compound I can be conveniently produced according to any of the following methods 1, 2 and 3 of the invention.

METHOD 1

In the first method, a compound of the formula II:

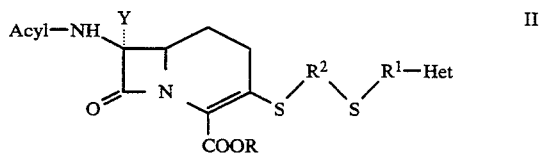

wherein Acyl, Het, R$^1$, R$^2$ and Y are as defined above and R is a hydrogen or a carboxy-protecting group is prepared by reacting a compound of the formula III:

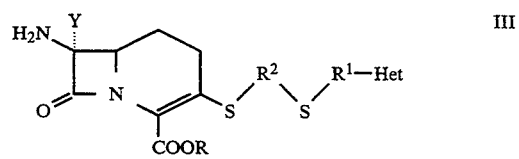

wherein Het, R, R$^1$, R$^2$ and Y are as defined above, or its reactive derivative with an acid of the formula:

Acyl-OH wherein Acyl is optionally protected acyl or its reactive derivative and the resulting compound II is deprotected to give a compound I of the invention.

METHOD 2

A compound of the formula IV:

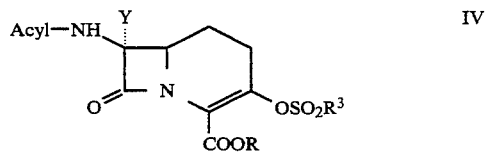

wherein Acyl, R and Y are as defined above and R$^3$ is alkyl or aryl, or its reactive derivative is reacted with a compound of the formula:

AcSR$^2$SR$^1$Het wherein Ac is acyl and Het, R$^1$ and R$^2$ are as defined above, or its reactive derivative to obtain a compound II, which is then deprotected to give a compound I of the invention.

METHOD 3

A compound of the formula V:

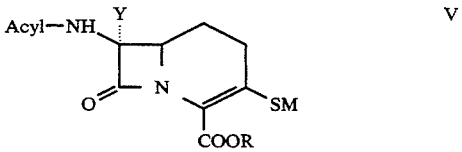

wherein Acyl, R and Y are as defined above and M is hydrogen or a heavy metal, or its reactive derivative is reacted with a compound of the formula:

Hal-R²SR¹Het wherein Hal is halogen and Het, $R^1$ and $R^2$ are as defined above, or its reactive derivative to obtain a compound II, which is then deprotected to give a compound I of the invention.

All the required starting materials for the above methods, that is, compounds having 1-carba-3-cephem nucleus, 7-side chain acids and 3-substituents, are prepared, for example, according to the processes described in the Preparation Example below. However, the method of the present invention is by no means restricted to the use of starting compounds prepared by the procedures herein described but can be effected using any equivalent compounds obtained by methods known to one of ordinary skill in the art.

The outline of each method is described below.

An acyl group is introduced at the 7-position cf a cephem nucleus by amidation where an amine or its reactive derivative is reacted with a carboxylic acid or a reactive derivative thereof.

The amidation is generally carried out using a slight excess of acid in an appropriate solvent in the presence of condensing agent at a temperature ranging from about −30 to 50° C., preferably about −10 to 30° C. for about 10 min to 10 hr, preferably about 30 min to 2 hr.

Examples of condensing agents include carbodiimides such as N,N'-diethylcarbodiimide, N,N'-dicyclohexylcarbodiimide and the like; carbonyl compounds such as carbonyldiimidazole and the like; isoxazolinium salts; acylamino compounds such as 2-ethoxy-1-ethoxycarbonyl-1,2-dihydroquinoline and the like; halogenated phosphoric acids; sulfonyl halides; amidated enzymes and the like.

Preferably, an amine is reacted with 1–2 equivalents of a carboxylic acid in the presence of 1–2 equivalents of a condensing agent(s) in a solvent free from an active hydrogen such as dichloromethane, chloroform, ethyl acetate, acetonitrile or the like.

The reactive derivatives of an amine include compounds whose 7-amino group is activated with the aid of various groups, for example, silyl group such as trimethyl silyl, methoxydimethyl silyl, t-butyldimethylsilyl and the like; stannyl group such as trimethylstannyl and the like; alkylene group through which the amino group binds to alkanal, acetone, acetylacetone, acetoacetate ester, acetoacetoanilide, acetacetonitrile, cyclopentanedione, acetylbutylolactone and the like to form enamine; alkylidene group such as 1-haloalkylidene, 1-haloaralkylidene, 1-alkoxyalkylidene, 1-alkoxyaralkylidene, 1-alkoxy-1-phenoxyalkylidene, alkylidene, aralkylidene and the like; acid such as mineral acid, carboxylic acid, sulfonic acid and the like, with which the amino group forms a salt; acyl which is easy to remove such as alkanoyl and the like; or other reactive $C_1$–$C_{10}$ groups useful for such purpose. Reactive derivatives of an amine also include compounds wherein functional groups other than 7-amino group have been protected.

Examples of the reactive derivatives of carboxylic acid include acid anhydrides, for instance, symmetric or mixed anhydride [mixed acid anhydride with mineral acid (phosphoric acid, sulfuric acid, half ester of carbonic acid and the like), organic acid (alkanoic acid, aralkanoic acid, sulfonic acid and the like)]; intramolecular anhydride (ketene, isocyanate and the like); acid halide (mixed acid anhydride with hydrogen halide); acid halide; active ester [enol ester (vinyl ester, isopropenyl ester and the like), aryl ester (phenyl ester, halophenyl ester, nitrophenyl ester and the like), heterocyclic ester (pyridyl ester, benzotriazolyl ester and the like), ester of N-hydroxy compound, ester of diacylhydroxylamine (N-hydroxysuccinimidoyl ester, N-hydroxyphthalimidoyl ester and the like), thiol ester (aralkylthiol ester, heterocyclic thiol ester and the like)]; active amide (aromatic amide formed with imidazole, triazole, 2-ethoxy-1,2-dihydroquinoline or the like, or diacylanilide).

The above-mentioned reactive derivatives of amine and/or carboxylic acid are reacted in the presence of acid capturing reagents including inorganic bases (oxides, hydroxides, carbonates, hydrocarbonates or the like of alkali metals or alkaline earth metals); organic bases (tertiary amine, aromatic amine and the like); oxiranes (alkylene oxide, aralkylene oxide and the like); pyridinium salts (tripyridiniumtriazine trichloride and the like); adsorbents (Celite and the like).

Preferably, the amine is reacted with 1–2 mol of a reactive derivative of carboxylic acid (Acyl-OH) and 0–2 mol of an acid capturing agent in an inert solvent free from an active hydrogen. The reaction between an enzymatic ester and an acid halide proceeds even in an aqueous solvent.

After the reaction is complete, the reaction mixture is neutralized with acid, extracted with a solvent, and concentrated. The residue, when purified by, for example, recrystallization from a solvent or column chromatography, gives a protected product II, which is then deprotected conventionally to yield the objective compound I.

One of the starting compounds of the method 2, a compound of formula IV, can be, for example, prepared by the amidation of a corresponding compound having amino group at the 7β-position by any methods generally used in the art as described above.

The other starting compound, an acylthioalkylthio compound (AcSR²SR¹Het), can be prepared by treating a corresponding heterocyclic thiol with sodium hydride at a temperature ranging from about −30 to 30° C. in a solvent such as dimethylformamide and the like to give alkali metal mercaptide and reacting the mercaptide with halomethyl thiolcarboxylate.

Alternatively, an acylthiomethyl compound, AcSR²SR¹Het, can be prepared by reacting an alkali metal heterocyclic mercaptide with a reagent such as bromochloromethane to give a compound of the formula: ClR²SR¹Het, and treating the latter with a thiolcarboxylate salt.

The reaction between a compound IV and an acylthioalkylthio compound can be conducted preferably by reacting the compound VI with an equal to excess amount, preferably 1–10 equivalent, more preferably 1–3 equivalent amount, of acetyl- or benzoyl-thiomethylthio derivative in an appropriate-solvent in the presence of a base such as sodium methoxide at a temperature ranging from about −90° to 50° C., preferably about −80° to −10° C. for about 5 min to about 20 hr, preferably about 0.3 hr to about 7 hr. Any ordinary organic solvents except for acidic ones can be used. Examples of especially preferred solvents are tetrahydrofuran, dimethylformamide, acetonitrile, dimethylacetoamide, hexamethylphosphoramide, dimethylsulfoxide, methanol, ethanol, propanol and the like.

The same objective compound can be obtained by reacting a compound IV with an alkali metal thioalkylthio derivative prepared by reacting an acylthioalkylthio compound with an alkali metal alkoxide.

After the reaction is complete, the reaction mixture is neutralized with an acid such as hydrochloric acid or acetic acid, diluted with water and extracted with an appropriate solvent. Examples of extracting solvents include ethyl acetate, dichloromethane and the like.

The extract is then dried, concentrated under reduced pressure and the residue is purified appropriately by, for example, extraction, washing, recrystallization, or column chromatography on silica gel. Examples of solvents for the recrystallization are toluene, ethyl acetate, acetonitrile, dichloromethane, methanol and the like. Examples of eluents for chromatography are a mixture of toluene and ethyl acetate and the like. The product, when deprotected, gives the desired compound of formula I.

The starting material of the method 3, a compound V, may be a salt of metal such as silver or an organic base such as pyridine, with a preference for the silver salt. The halogen atom of the methylthiomethyl halide can be chlorine, bromine or iodine, with a preference for iodine.

A compound V can be prepared from an appropriate starting material including compounds IV as follows. Thus, a 3-thiol derivative is prepared from compound IV and is converted into a salt, preferably silver salt.

A 3-thiol compound can be prepared by reacting a solution of 3-sulfonyloxy compound in an appropriate solvent with sodium hydrosulfide at a temperature ranging from about −40° to 0° C. for about 30 to 60 min, neutralizing with acid such as hydrochloric acid and extracting with an appropriate organic solvent such as ethyl acetate. The extract is dried and concentrated to yield the objective 3-thiol. Examples of appropriate reaction solvents are dimethylformamide, acetonitrile and the like.

A silver salt of 3-thiol can be obtained by contacting a thiol with a slightly excess amount of silver nitrate in an appropriate solvent at about −30° to 20° C. for about 10 to 30 min. Examples of solvents are tetrahydrofuran, dichloromethane and the like. The silver salt can be separated by diluting the reaction mixture with water, extracting with dichloromethane and concentrating the extract.

The halogenated alkylthio derivative of the formula: Hal-$R^2SR^1$Het can be prepared by reacting a corresponding heterocyclic thiol with bromochloromethane in a solvent such as dimethylformamide in the presence of a base such as sodium hydride. If necessary, the resulting chloromethylated product is reacted with sodium iodide for the iodine replacement.

The reaction between a compound V and a 2-halogenated alkylthio derivative is carried out in an appropriate solvent at a temperature ranging from about 0° to 30° C. for about 2 to 20 hr. Examples of appropriate solvents are hexamethylphosphorotriamide, dimethylformamide and the like. The product is extracted with an organic solvent such as ethyl acetate and the extract is concentrated. The residue is purified by, for example, column chromatography on silica gel.

As the final step, the product II is deprotected to yield the compound I.

Deprotection of protected carboxy group can be carried out in an inert solvent by any of conventional methods. For example, when the carboxy-protecting group is a reactive ester-forming group, deprotection can be carried out by treating the protected product in an inert solvent with acid, base, buffer solution, ion-exchanging resin or the like. In case of an insufficiently reactive ester-forming group, the deprotection can be effected after an appropriate activation. Thus, trichloroethyl esters can be activated with metal and acid; p-nitrobenzyl esters can be activated by hydrogenation or treatment with salts of dithionic acid, or a metal and an acid; phenacyl esters are activated by radiation of light. Carboxy-protecting groups which are aralkyl can be removed by catalytic hydrogenation on palladium, platinum, nickel and the like. Carboxy-protecting groups which are tertiary alkyl, cyclopropylmethyl, 2-alkenyl, aralkyl, sulfonylethyl can be removed by treating the product with an acid in the presence of a cation-scavenger such as anisole, benzenethiol and the like, if necessary. Examples of acids include mineral acids; Lewis acids such as aluminum chloride, stannic chloride, titanium tetrachloride and the like; sulfonic acids such as benzenesulfonic acid, methanesulfonic acid, trifluoromethanesulfonic acid and the like; strong carboxylic acids such as trifluoroacetic acid and the like. When the carboxy-protecting group is 2-alkenyl, it can be removed by treating the product with triarylphosphine-palladium chelate compounds. When the carboxy-protecting group is phenacyl, 2-alkenyl, hydroxyaralkyl or the like, it can be removed by treating the product with an alkali or a nucleophilic reagent. As is evident to one of ordinary skill in the art, any other equivalent deprotecting methods are also available.

Deprotection of protected hydroxy group can be carried out in a conventional manner. For example, an ether bond is cleaved by reacting the hydroxy-protected compound with an acid, for example, a Lewis acid such as aluminum chloride, stannic chloride or titanium tetrachloride, a strong carboxylic acid such as trifluoroacetic acid or the like, optionally in the presence of a cation scavenger such as anisole, benzenethiol. The reaction is usually carried out in a solvent at −10° C. to 50° C. for 30 min to 10 hr to give the objective hydroxy compound.

Deprotection of protected amino group can be carried out by any of conventional methods depending on the kinds of the protecting group as follows.

1) Alkoxycarbonyl (t-butoxycarbonyl, etc.) or the like: treatment with a strong acid (trifluoroacetic acid, trifluoromethanesulfonic acid, etc.), Lewis acid (aluminum chloride, stannic chloride, titanium chloride, zinc chloride, etc.) or other acids, if required, in the presence of a cation scavenger such as anisole, benzenethiol or the like.

2) Aralkoxycarbonyl (carbobenzoxy, methylcarbobenzoxy, diphenylmethoxycarbonyl, etc.) or the like: treatment with a Lewis acid and a cation scavenger or hydrogenation catalyzed by palladium or nickel or the like.

3) Lower alkanoyl (formyl, acetyl, chloroacetyl, etc.), Schiff base forming group (a divalent carbon group, e.g., ethylidene, propylidene, benzylidene, substituted benzylidene, etc.), aralkyl (trityl, substituted trityl, etc.), arylthio (phenylsulfenyl, etc.), tetrahydropyranyl, silyl or stannyl (trimethylstannyl, trimethylsilyl, etc.), or the like: treatment with an acid such as hydrochloric acid, sulfuric acid, methanesulfonic acid or the like.

4) Others: a method specific for individual protecting group should be selected. For example, thiourea is specific for haloacetyl or N-alkyldithiocarbamate amino-protecting group, hydrazine for dibasic acid acyl and phosphorus pentachloride and alkanol for amide.

Methods for deprotection as described above and those analogous to them are described in literatures such as "Protective Groups in Organic Chemistry" J.F.W. Ed., McOmie, pp.183 (1973), Pleum PLUM Press, N.Y.; "The Chemistry of Functional Groups" S. Patai, Ed., (1969), Interscience Publ., John Wiley & Sons Ltd. London; "Cephalosporins and Penicillins" Flynn Ed., Academic Press, N.Y. (1972).

The resulting free acid I is then converted into pharmaceutically acceptable salts, if desired, in a conventional manner. Preferably, bases used to form such salts are light metals commonly used in the field of cephalosporin antibiotics, which can render a physiologically acceptable ion, for example, lithium, sodium, potassium, magnesium, aluminium and the like. Further, $C_1$-$C_{12}$ alkylammoniums such as trimethylammonium, triethylammonium, methylmorpholinium or $C_4$-$C_9$ aromatic bases such as pyridinium, collidinium, picolinium, quinolinium, dimethylanilinium and the like are also preferred.

Furthermore, a free acid of formula I can form an ester having antibacterial activities on oral and parenteral administration with a $C_2$-$C_{15}$ pharmaceutically active ester-forming group as mentioned above.

Salts can be obtained by reacting a free acid I with a base or a weak carboxylic acid salt of a base in a conventional manner. For example, an acid I is neutralized with a base such as hydroxide, carbonate or bicarbonate of a light metal, or subjected to an exchange decomposition with a salt of lower carboxylic acid such as sodium acetate, sodium lactate or sodium 2-ethylhexanoate in a polar aromatic-solvent such as alcohol, ketone, ester or the like. The resulting salt can be isolated by separating out by diluting the reaction mixture with an appropriate solvent in which the salt hardly or slightly dissolves, or by lyophilization.

The reaction generally is complete within about 1 to 10 min at a temperature lower than about 50° C. When no side reactions are observed, the reaction may be allowed to continue for an additional period of time.

The salts of the compound I, when neutralized, give the compound I of the invention. Accordingly, the present invention further provides a method for producing the compound I by neutralizing a salt of compound I with an acid.

When compound I has a basic group such as amino, an acid addition salt can be obtained by reacting the compound I with an acid such as hydrochloric acid, acetic acid or the like in a manner conventional in the field of cephalosporin, which salt in turn can be converted into a compound of formula I having a free amino group(s), if necessary. Thus, a compound I having a free amino group is reacted with about 1 to 2 moles of an acid at about 0° to 50° C. for about 10 to 90 min. The neutralization can be carried out by reacting the salt with about 1 to 2 moles of a base under conditions similar to those mentioned above.

The reactions in methods 1, 2 and 3 are carried out at a temperature ranging from about −80° to 100°, preferably from about −40° to 50° C. for about 10 min -20 hr, in general. When the product is stable, the reaction time can be prolonged. To each reaction is optionally applicable any conditions conventionally used in the art including reaction solvent, anhydrous condition, inert gas introduction and/or stirring.

Examples of reaction solvents usable are hydrocarbons (pentane, hexane, octane, benzene, toluene, xylene and the like); halogenated hydrocarbons (dichloromethane, chloroform, carbon tetrachloride, dichloroethane, trichloroethane, chlorobenzene and the like); ethers (diethyl ether, methylisobutyl ether, dioxane, tetrahydrofuran and the like); ketones (acetone, methyl ethyl ketone, cyclohexanone and the like); esters (ethyl acetate, isobutyl acetate, methyl benzoate and the like); nitro hydrocarbons (nitromethane, nitrobenzene and the like); nitriles (acetonitrile, benzonitrile and the like); amides (formamide, acetamide, dimethylformamide, dimethylacetamide, hexamethylphosphoramide and the like); sulfoxides such as dimethylsulfoxide and the like; carboxylic acids (formic acid, acetic acid, propionic acid and the like); organic bases (diethylamine, triethylamine, pyridine, picoline, collidine, quinoline and the like); alcohols (methanol, ethanol, propanol, hexanol, octanol, benzylalcohol and the like); water; and other series of industrial solvents, or a mixture thereof.

To isolate the objective compound, the reaction mixture is subjected to the removal of contaminants such as unreacted starting materials, by-products or solvents in a conventional manner, for example, extraction, evaporation, washing, concentration, precipitation, filtration, drying and the like, which is followed by the work-up process using one or more procedures commonly used in the art, for example, adsorption, elution, distillation, precipitation, recrystallization, chromatography and the like.

Thus, the present invention also provides a process for producing a compound of formula I which comprises an introduction of 3-substituent and 7-acyl, esterification of 4-carboxylic acid, deprotection, salt-formation, neutralization or the like. Structural variants can be obtained by introducing substituent(s) at the cephem nuclei.

Although the above-mentioned methods 1, 2 and 3 are preferable for the production of the compound I, the present invention is not limited to compounds prepared by these methods, but all the compounds I prepared by any other methods known to one of ordinary skill in the art fall within the scope of the present invention.

The compound of the invention, when evaluated in vitro for the antibacterial activity, proved to be highly effective against gram-positive bacteria such as *Staphylococcus aureus* and *Streptococcus pyogenes* and gram-negative bacteria such as *Klebsiella pneumoniae, Proteus, Morgania morganii, Enterobacter cloacar, Serratia marcescens, Escherichia coli* and the like.

The absorption rate of the compound of the invention on oral administration was also evaluated in mice by measuring the blood level following administration. The result indicated a high blood level of a compound I, showing the effectiveness of the compound I on oral administration.

Thus, the present invention provides a method for combating bacteria by bringing the bacteria into contact with an effective amount of compound I. The compounds of the invention can be applied to a wide range of subjects such as not only animals including human beings infected with sensitive bacteria, but also perishable materials, instruments to be disinfected and the like.

The present invention also provides a pharmaceutical formulation for the treatment or prophylaxis of bacterial infections, which comprises a pharmaceutically effective amount of a compound of formula I, a salt thereof, or an amino-, carboxy- and/or hydroxy-protected derivative thereof.

When the compound I of the invention is used for treatment, an effective amount of a compound of formula I or a derivative thereof such as a salt is administered to a subject animal including human orally or parenterally. The oral administration is preferable. For the oral administration, a compound I can be formulated in standard formulations such as capsules, tablets, powders, granules or the like together with pharmaceutically acceptable carriers, diluents or excipients. For the parenteral administration, a compound I is formulated in subcutaneously, intramuscularly, intravenously, or intraperitoneally injectable solutions or suspensions. It also can be formulated into ointment, suppository, liniment and the like.

Suitable daily dose for a compound of formula I can be between about 10 mg and about 4000 mg, preferably about 100 mg and about 2000 mg on oral administration, and about 10 mg and about 4000 mg, preferably about 50 mg and about 2000 mg on parenteral administration.

The following Examples are provided to further illustrate the present invention and are not to be construed as limiting thereof.

Abbreviations used in the Examples are explained below:Ac, acetyl group; BH, diphenylmethyl group; Boc, t-butoxycarbonyl group; Et, ethyl group; Me, methyl group; Ms, methansulfonyl group; Ph, phenyl group; PMB, p-methoxybenzyl group; Tr, trityl group; DMF, dimethylformamide; and THF, tetrahydrofuran.

EXAMPLE 1

7β-[(Z)-2-(2-Aminothiazol-4-yl)-2-hydroxyiminoacetamido]-3-(1,2,3-triazol-4-ylthiomethylthio)-1-carba-3-cephem-4-carboxylic acid

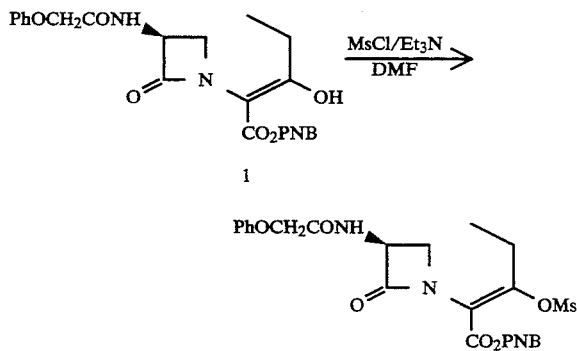

To a solution of Compound 1 (p-nitrobenzyl 7β-phenoxyacetamido-3-hydroxy-1-carba-3-cephem-4-carboxylate) (11.53 g, 3.28 mmol) in dimethylformamide (15 ml) are added methanesulfonyl chloride (0.37 ml, 4.78 mmol) and triethylamine (0.62 ml, 4.45 mmol) at −40° C. and the mixture is stirred for 30 min at the same temperature. The reaction mixture is diluted with water and extracted with ethyl acetate. The extract is washed with brine, dried over sodium sulfate and concentrated. The residue, when purified by chromatography on silica gel (toluene/ethyl acetate=1:1), gives Compound 2 (p-nitrobenzyl 7β-phenoxyacetamido-3-methanesulfonyloxy-1-carba-3-cephem-4-carboxylate) (1.10 g; yield, 62%) as colorless foam.

Compound 2

1H-NMR δ(CDCl$_3$) ppm:8.24–8.20 and 7.62–7.58(4H, AA'BB'), 7.40–6.87(6H, m), 5.47–5.41(1H, m), 5.40 and 5.30(2H, ABq, J=13.0 Hz), 4.55(2H, s), 3.96(1H, ddd, J=3.8 Hz, J=5.1 Hz, J=12.7 Hz), 3.22(3H, s), 2.9–2.55(2H, m), 2.1–1.95(1H, m), 1.8–1.5(1H, m).

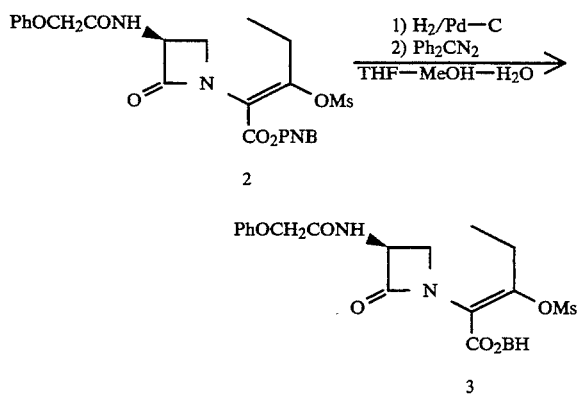

To a suspension of Compound 2 (870 mg, 1.60 mmol) in a mixture of tetrahydrofuran (8 ml), methanol (8 ml) and water (8 ml) is added 10 % palladium on carbon (40 mg) and the mixture is stirred for 1.5 hr at room temperature in an atmosphere of hydrogen. Stirring is continued for another 1.5 hr at room temperature after the addition of diphenyldiazomethane (920 mg, 4.74 mmol). The reaction mixture is filtered and extracted with ethyl acetate. The extract is washed with brine, dried over sodium sulfate and concentrated. The residue, when purified by chromatography on silica gel (toluene/ethyl acetate=2:1), gives Compound 3 (diphenylmethyl 7β-phenoxyacetamindo-3-methanesulfonyloxy-1-carba-3-cephem-4-carboxylate) (921 rag; yield, quantitative) as yellow foam.

Compound 3

1H-NMR δ(CDCl$_3$) ppm: 7.5–6.85(17H, m), 5.45(1H, dd, J=5.0 Hz, J=7.5 Hz), 4.55(2H, s), 3.96(1H, ddd, J=3.5 Hz, J=5.0 Hz, J=11.5 Hz), 2.90(3H, s), 2.85–2.5(2H, m), 2.1–1.9(1H, m), 1.75–1.45(1H, m).

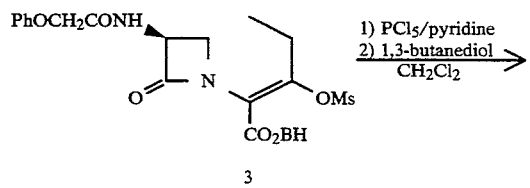

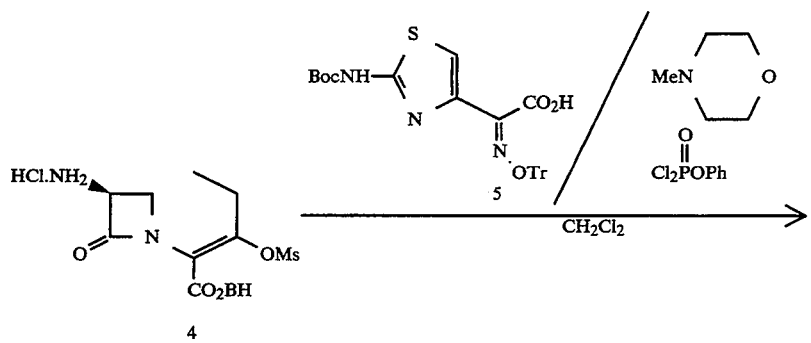

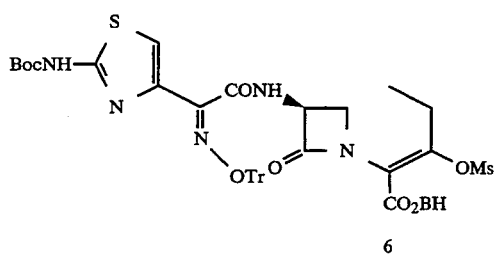

To a solution of Compound 3 (894 mg, 1.55 mmol) in dichloromethane (10 ml) are added pyridine (0.25 ml, 3.09 mmol) and phosphorus pentachloride (582 mg, 2.79 mmol) under ice-cooling. The mixture is stirred for 10 min at the same temperature and for 30 min at room temperature. The reaction solution is added dropwise to a −30° C. solution of 1,3-butanediol (0.84 ml, 9.37 mmol) in dichloromethan (3 ml) and the mixture is stirred for 5 min at −20° to −30° C. and for 30 min at room temperature. The reaction solution is diluted with dichloromethane. The resultant solution is washed with brine, dried over sodium sulfate and concentrated. The residue is washed with ether, precipitated, filtered, and dried to obtain crude Compound 4 (diphenylmethyl 7β-amino-3-methanesulfonyloxy-1-carba-3-cephem-4-carboxylate hydrochloride) (800 mg) as yellow powder.

Crude compound 4 (800 mg) and Compound 5 ((Z)-2-(2-t-butoxycarbonylaminothiazol-4-yl)-2-trityloxyimino carboxylic acid) (1.23 g, 2.33 mmol) are dissolved in dichloromthane (10 ml). To the solution are added N-methylmorpholine (0.61 ml, 5.55 mmol) and phenylphosphoric acid dichloride (0.28 ml, 1.87 mmol) and the mixture is stirred for 2 hr at the same temperature. The reaction solution is diluted with ethyl acetate. The resultant solution is washed with a diluted hydrochloric acid, a 5% solution of sodium hydrogen carbonate, and a brine, dried over sodium sulfate and concentrated. The residue, when purified by chromatography on silica gel (toluene/ethyl acetate=5:1), gives Compound 6 (diphenylmethyl 7β-[(Z)-2-(2-t-butoxycarbonylaminothiazol-4-yl)-2-trityloxyiminoacetamido]-3-methanesulfonyloxy-1-carba-3-cephem-4-carboxylate) (891 mg; yield, 60% on the basis of Compound 3).

COMPOUND 6

$^1$H-NMR δ(CDCl$_3$) ppm: 8.5–8.25(1H, brs) , 7.5–7.2 (26H, m), 7.02(1H, s), 6.94(1H, s), 5.47(1H, dd, J=5.0 Hz, J=6.2 Hz), 3.95(1H, ddd, J=3.7 Hz, J=5.0 Hz, J=11.8 Hz), 2.85(3H, s), 2.7–2.3(2H, m), 2.0–1.8 (1H, m), 1.55–1.3(1H, m), 1.50(9H, s).

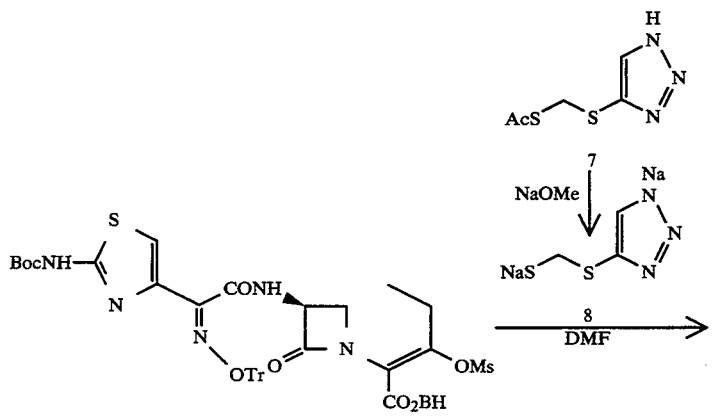

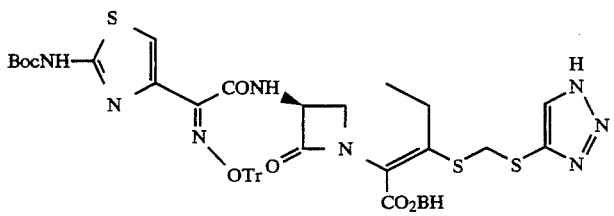

9

Compound 7 (4-(acetylthiomethylthio)-1,2,3-triazol) (213 rag, 1.13 mmol) is dissolved in dimethylformamide (5 ml) and cooled to −60° C. To the solution is added 1.26N solution of sodium methoxide in methanol (1.76 ml, 2.22 mmol) and the mixture is stirred for 30 min at −55° to −60° C. to give a solution of Compound 8 (disodium 4-acetylthiomethylthio)-1,2,3-triazol). To the solution is added a solution of Compound 6 (881 mg, 0.924 mmol) in dimethylformamide (3 ml) at −78° C. and the mixture is stirred for 1.5 hr at the same temperature and for 40 min at −60° to −70° C. After neutralization with 10% hydrochloric acid, the solution is diluted with water and extracted with ethyl acetate. The extract is washed with brine, dried over sodium sulfate and concentrated. The residue, when purified by chromatography on silica gel (toluene/ethyl acetate=2:1), gives Compound 9 (diphenylmethyl 7β-[(Z)-2-(2-t-butoxycarbonylaminothiazol-4-yl)-2-trityloxyimino acetamido]-3-(1,2,3-4-ylthiomethylthio)-1-carba-3-cephem-4-carboxylate) (628 mg; yield, 68%) as yellow foam.

Compound 9

$^1$H-NMR δ(CDCl$_3$) ppm: 7.56(1H, s), 7.53–7.2(26H, m), 7.04(1H, s), 6.91(1H, s), 5.42(1H, dd, J=5.0 Hz, J=6.7 Hz), 4.02(2H,s), 3.81(1H, ddd, J=3.3 Hz, J=5.0 Hz, J=11.7 Hz), 2.5–2.1(2H, 1.85–1.65(1H, m), 1.51(9H, s), 1.5–1.2(1H, m).

washing is re-extracted with water. The aqueous solutions obtained by the dilution and re-extraction are combined and loaded onto a column of styrene-divinylbenzene copolymer resin (HP-20) (Mitsubishi Kasei, Japan) and the column is eluted with methanol/water=4:1. The resultant powder, when washed with ethyl acetate and concentrated, gives Compound 10 (238 mg, yield, 79%) as pale yellow powder.

Compound 10

$^1$H-NMR δ(D$_2$O+NaHCO$_3$) ppm: 7.99(1H, s), 6.92(1H, s), 5.50(1H, d, J=4.6 Hz), 4.25 and 4.06(2H, ABq, J=13.7 Hz), 4.0–3.85(1H, m), 2.6–2.3(2H, m), 2.2–2.0(1H, m), 1.8–1.5(1H, m).

IR ν (KBr) cm$^{-1}$: 3100 (br), 1745, 1640, 1605, 1525, 1390, 1375, 1350.

Assay for the evaluation of in vitro and in vivo activity of compound I

The in vitro antibacterial activity of a compound as prepared in the foregoing Example was evaluated as follows. A compound to be tested was dissolved in 0.01N aqueous solution of sodium hydrogen carbonate and the solution was applied to an agar plate and the minimal inhibitory concentration (MIC) against each bacterium was measured by two-fold dilution method according to the standard method of the Japan Society of Chemotherapy.

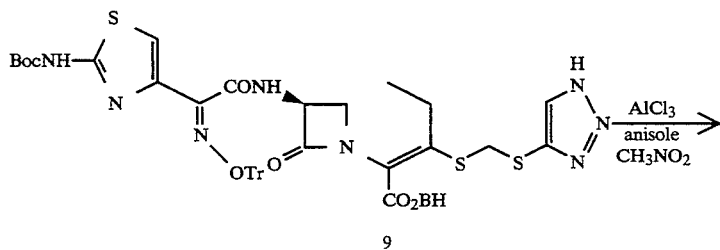

9

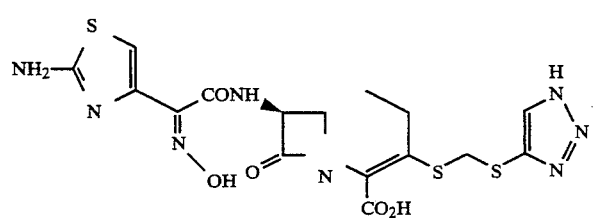

10

To a solution of Compound 9 (609 mg, 0.607 mmol) in a mixture of anisole (3 ml) and nitromethane (12 ml) is added a solution of aluminum chloride (645 mg, 4.85 mmol) in anisole (3 ml) at −40° C. and the mixture is stirred for 40 min at −30° to −40° C. After the addition of 1N hydrochloric acid (5 ml), the reaction mixture is diluted with water and washed with ethyl acetate. The The in vivo pharmacokinetics was also investigated in mice by measuring the blood level at 3 hr after administrating a test compound to a mouse (10 mg/kg).

In the assay, as a control compound, 7β-[(Z)-2-(2-amino-4-thiazolyl)-2-hydroxyiminoacetamido]-3-(1,2,3- triazol-4-yl)thiomethylthio-3-cephem-4-carboxylic acid (a thiomethylthio cephalosporin disclosed in U.S. patent application Ser. No. 07/729,413, filed on Jul. 12, 1991, now U.S. Pat. No. 5,214,037, and EPO Application Publication No. 0 467 647 A2) was used.

Results are shown in Tables 1 and 2 below. In the tables, Compound A is a compound of the invention and Compound B is a control compound.

TABLE 1

In Vitro Antibacterial Activity

| Bacterium | MIC (μg/ml) | |
| --- | --- | --- |
|  | Compound A | Compound B |
| E. coli JC-2 | 0.05 | 0.3 |
| E. coli EC-14 | 0.025 | 0.1 |
| E. coli SR377 | 0.2 | 0.8 |
| E. coli SR73 | 0.39 | 1.6 |
| K. pneumoniae SRI | 0.025 | 0.1 |
| E. cloacae SR233 | 0.1 | 0.8 |
| E. cloacae ATCC 13047 | 12.5 | 100 |
| S. maecescense ATCC 13880 | 0.2 | 3.2 |

E. cloacae: Enterobacter cloacae; and S. marcescense: Seratia marcescense.

TABLE 2

In Vivo Pharmacokinetics

|  | Compounf A | Compound B |
| --- | --- | --- |
| Binding ability to plasma proteins* | 90% | 96% |
| Blood level (3 hour) | 82 μg/ml | 18 μg/ml |

*: tentative value

Medical formulations

| 1. | Granules | |
| --- | --- | --- |
|  | 7β-[(Z)-2-(2-t-Aminothiazol-4-yl)-2-hydroxyiminoacetamido]-3-(1,2,3-triazol-4-ylthiomethylthio)-1-carba-3-cephem-4-carboxylic acid | 100 mg |
|  | lactose | 600 mg |
|  | corn starch | 290 mg |
|  | hydroxypropylcellulose | 10 mg. |

Above materials are granulated by wet-method and 1 g each is packaged as granule formulation, which can be administered three times a day to a patient suffering from infection caused by sensitive bacteria.

| 2. | Hard capsules | |
| --- | --- | --- |
|  | 7β-[(Z)-2-(2-t-Aminothiazol-4-yl)-2-hydroxyiminoacetamido]-3-(1,2,3-triazol-4-ylthiomethylthio)-1-carba-3-cephem-4-carboxylic acid | 100 mg |
|  | corn starch | 47 mg |
|  | magnesium stearate | 1.5 mg |
|  | talcum powder | 1.5 mg. |

Above materials are granulated in a conventional manner and filled in hard gelatine capsules of size No. 4, which can be administered three times a day to a patient suffering from infection caused by sensitive bacteria.

Above materials are granulated in a conventional wet method and formulated with a tabletting machine to give tablets of diameter 7.5 mm, which can be administered three times a day to a patient suffering from infection caused by sensitive bacteria.

We claim:

1. A compound of the formula I:

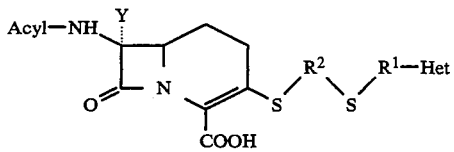

wherein Acyl is $C_1$–$C_{12}$ acyl; Het is a 5- or 6-membered ring containing one or more hetero atoms selected from nitrogen and sulfur optionally substituted by lower alkyl; $R^1$ is a single bond or $C_1$–$C_4$ alkylene; $R^2$ is a straight or branched $C_1$–$C_4$ alkylene; and Y is a hydrogen atom or methoxy group, or a pharmaceutically acceptable salt thereof.

2. The compound as claimed in claim 1 wherein Acyl is $C_1$–$C_8$ alkanoyl, $C_7$–$C_{11}$ aroyl, 5- to 6-membered homocyclic aralkanoyl, or 5- to 6-membered heterocyclic aralkanoyl, each of which is optionally substituted by substitutents selected from the group consisting of haloalkylthio, alkoxyimino, cyclic alkoxyimino, alkenyloxyimino, amino, protected amino, hydroxy, oxo, hydroximino, protected hydroxyimino, carboxyalkoxyimino and carboxyalkenyloxyimino.

3. The compound as claimed in claim 1 wherein Acyl is 2-(2-aminothiazol-4-yl)-2-hydroxyiminoacetyl wherein the hydroxyimino group is optionally modified with a hydroxy-protecting group, $C_1$–$C_5$ alkyl or $C_2$–$C_5$ carboxyalkyl.

4. The compound as claimed in claim 1 wherein Het is a five membered heteroaromatic group containing 3 to 4 hetero atoms selected from nitrogen and sulfur.

5. The compound as claimed in claim 1 wherein Het is pyridyl, pyridyl substituted with $C_1$–$C_5$ alkyl, triazolyl, triazolyl substituted with $C_1$–$C_5$ alkyl, thiadiazolyl, thiadiazolyl substituted with $C_1$–$C_5$ alkyl, tetrazolyl or tetrazolyl substituted with $C_1$–$C_5$ alkyl.

6. The compound as claimed in claim 1 wherein Het is 1,2,3- triazolyl substituted with methyl.

7. The compound as claimed in claim 1 wherein $R^1$ is a single bond.

8. The compound as claimed in claim 1 wherein $R^2$ is methylene.

9. The compound as claimed in claim 1 wherein Y is hydrogen.

10. The compound as claimed in claim 1 wherein $R^1$ is a single bond; $R^2$ is methylene; Het is 1,2,3-triazolyl optionally substituted with methyl; Y is hydrogen; and Acyl is 2-(2-aminothiazol-4-yl)-2-hydroxyiminoacetyl.

11. A pharmaceutical formulation which comprises a pharmaceutically effective amount of a compound as claimed in claim 1 as an active ingredient in association with a pharmaceutically acceptable carrier, diluent, or excipient therefor.

12. A method for combating bacteria which comprises bringing the bacteria into contact with an effective amount of a compound I as claimed in claim 1.

13. A method for treating bacterial infections caused by sensitive bacteria which comprises administering to subjects an effective amount of a compound as claimed in claim 1.

* * * * *